United States Patent [19]

Kurono et al.

[11] Patent Number: 4,897,495
[45] Date of Patent: Jan. 30, 1990

[54] PROCESS FOR THE PREPARATION OF PYRROLIZINE DERIVATIVES

[75] Inventors: Masayasu Kurono; Yasuaki Kondo; Ryoichi Unno; Yukiharu Matsumoto; Hiromoto Kimura; Mitsuru Oka; Kiichi Sawai, all of Aichi, Japan

[73] Assignee: Sanwa Kagaku Kenkyusho Co., Ltd., Aichi, Japan

[21] Appl. No.: 351,006

[22] Filed: May 12, 1989

[30] Foreign Application Priority Data

Jun. 7, 1988 [JP] Japan .................. 63-138406

[51] Int. Cl.⁴ .......................... C07D 487/02
[52] U.S. Cl. .................................. 548/453
[58] Field of Search .......................... 548/453

[56] References Cited

U.S. PATENT DOCUMENTS 3,544,590 12/1970 Kittleson ..................... 548/453

FOREIGN PATENT DOCUMENTS 61-229893 10/1986 Japan .
61-254587 11/1986 Japan .
62-16487 1/1987 Japan .

OTHER PUBLICATIONS

Miyano et al., "Abstract on the 97th Annual Lecture of the Pharmaceutical Society of Japan", p. 223, 1978.
Miyano et al., "Synthesis", p. 701, 1978.
Miyano et al., "J. Heterocyclic Chem.", vol. 19, p. 1465, 1982.

*Primary Examiner*—Mary C. Lee
*Assistant Examiner*—Robert C. Whittenbauch
*Attorney, Agent, or Firm*—Armstrong, Nikaido, Marmelstein, Kubovcik & Murray

[57] ABSTRACT

A process for the preparation of pyrrolizine derivatives of the formula

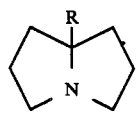

wherein R is —CN or —CH$_2$NH$_2$, and salts thereof.

1 Claim, No Drawings

PROCESS FOR THE PREPARATION OF PYRROLIZINE DERIVATIVES

BACKGROUND OF THE INVENTION

1. Field of the Invention

The present invention relates to a process for the preparation of pyrrolizine derivatives, and more particularly to a process for the preparation of 7a-aminomethyl-2,3,5,6,7,7a-hexahydro-1H-pyrrolizine and salts thereof, as well as a process for the preparation of 7a-cyano-2,3,5,6,7,7a-hexahydro-1H-pyrrolizine and salts thereof, as an intermediate for synthesizing said 7a-aminomethyl-2,3,5,6,7,7a-hexahydro-1H-pyrrolizine.

2. Related Arts

7a-Aminomethyl-2,3,5,6,7,7a-hexahydro-1H-pyrrolizine and 7a-cyano-2,3,5,6,7,7a-hexahydro-1H-pyrrolizine shown by the following formulae (1-B and 1-A) have been known as useful compounds for preparing various pharmaceutical and agricultural medicines, since those have an alkaroid skeletone therein.

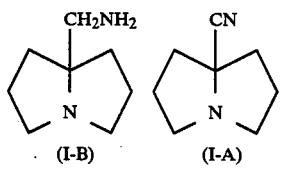

Further, each of the compounds can also be employed as the raw material for synthesizing organoplatinum complexes [Jap. Pat. No. Sho 61-229893(A)], 2-oxopyrrolidine compounds and salts thereof [Jap. Pat. No. Sho 61-254587(A)] as well as cephalosporin derivatives [Jap. Pat. No. Sho 62-16487(A)].

As far as the synthesis of 7a-aminomethyl-2,3,5,6,7,7a-hexahydro-1H-pyrrolizine is concerned, hitherto, only one method has been known, wherein 7a-cyano-2,3,5,6,7,7a-hexahydro-1H-pyrrolizine is reduced with use of lithium aluminum hydride [Miyano et al. "Abstract on the 97th Annual Lecture of the Pharmaceutical Society of Japan", page 223 (1978)]. In this case, the raw material of 7-cyano-2,3,5,6,7,7a-hexahydro-1H-pyrrolizine has been prepared by reacting γ-butyrolactone with KOCN, thermally treating the resulting γ-(N-2-pyrrolidinonyl)butyric acid in the presence of soda lime, reacting the resulting 2,3,5,6-tetrahydro-1H-pyrrolizine with perchloric acid, and reacting the resulting 1,2,3,5,6,7-hexahydropyrrolizinium perchlorate with potassium cyanide [Miyano et al. "Synthesis", page 701 (1978)]. Such a process has also been proposed for preparing said γ-(N-2-pyrrolidinonyl)-butyric that γ-butyrolactone is added to a reaction mixture of 2-pyrrolidone and sodium [Miyano et al. "J. Heterocyclic Chem.", Vol. 19, page 1455 (1982)].

Further, it has been known as the process for the preparation of 7a-substituted-2,3,5,6,7,7a-hexahydro-1H-pyrrolizine derivatives that said 1,2,3,5,6,7-hexahydropyrrolizinium perchlorate is reacted with one of various nucleophilic reagents, or that the cyano group in said 7a-cyano-2,3,5,6,7,7a-hexahydro-1H-pyrrolizine is chemically modified or changed.

The following is summary of said related arts, shown by chemical formulae.

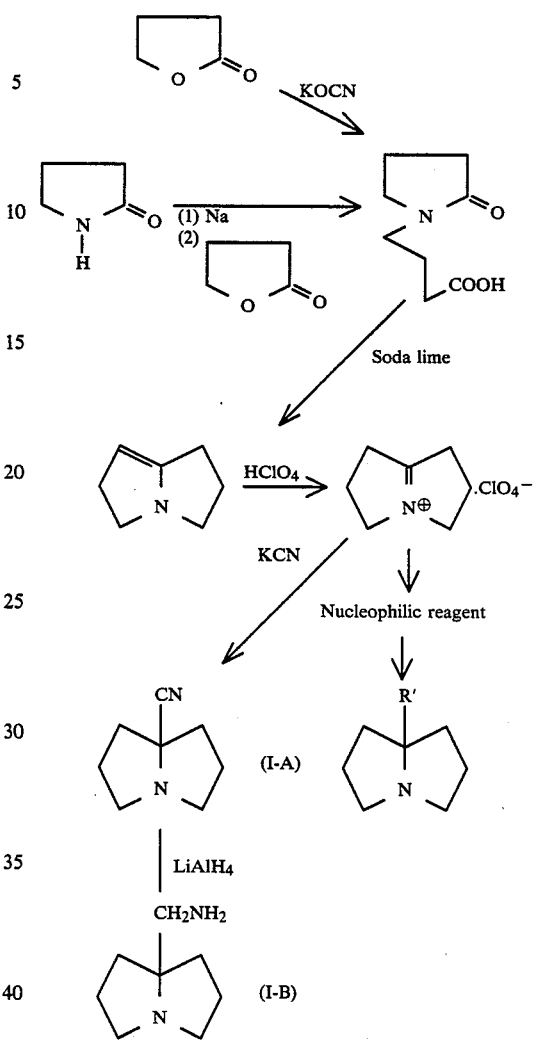

The conventional process for preparing 7a-aminomethyl-2,3,5,6,7,7a-hexahydro-1H-pyrrolizine as referred to, however, has disadvantages as stated below.

The first step of that γ-butyrolactone is reacted with KOCN to synthesize γ-(N-2-pyrrolidinonyl)butyric acid has problems in that a relatively high temperature (about 200° C.) is required for the reaction, and that yield of the product is somewhat low (about 40%). Such a process developed as another or separate method that after the reaction between 2-pyrrolidone and sodium, γ-butyrolactone is added to synthesize γ-(N-2-pyrrolidinonyl)-butyric acid has a problem in that there is possibility of causing an explosion or the like abnormal reaction.

The second step of that γ-(N-2-pyrrolidinonyl)-butyric acid is thermally treated in the presence of sodalime to synthesize 2,3,5,6-tetrahydro-1H-pyrrolizine has problems in that a relatively high temperature (about 250°–300° C.) is required for the reaction, and that the resulting compound has a relatively low stability.

Further, the final step of that 7a-cyano-2,3,5,6-tetrahydro-1H-pyrrolizine is reduced to synthesize 7a-aminomethyl-2,3,5,6,7,7a-hexahydro-1H-pyrrolizine has also problems of that an expensive lithium aluminum hydride is required as the reduction reagent, and that the reaction should be carried out in an anhydrous solvent.

Each of the processes, wherein 1,2,3,5,6,7-hexahydro-pyrrolizinium perchlorate is reacted with the nucleophilic reagent, or cyano group in 7a-cyano-2,3,5,6,7,7a-hexahydro-1H-pyrrolizine is chemically modified has the disadvantage of that a production of its starting material is difficult, as referred to.

SUMMARY OF THE INVENTION

An essential target of the invention lies, therefore, in establishment of a process for preparing the pharmacologically useful compound of 7a-aminomethyl-2,3,5,6,7,7a-hexahydro-1H-pyrrolizine and salts thereof, which is easy in synthetic operation, ensures a high safety in work, requires no expensive reagent, gives good yield, and is suitable for industrial scale production thereof.

Concrete objects of the invention are, in the first place, to provide a novel process for the preparation of 7a-cyano-2,3,5,6,7,7a-hexahydro-1H-pyrrolizine, in the next place, to provide a process for converting the compound into 7a-aminomethyl-2,3,5,6,7,7a-hexahydro-1H-pyrrolizine, which is advantageous in economical and other various view points.

According to the invention, the first concrete object can be attained by a process for the preparation of 7a-cyano-2,3,5,6,7,7a-hexahydro-1H-pyrrolizine and a salt thereof, which comprises a step for reacting 1,7-di-substituted-4-heptanone of the formula

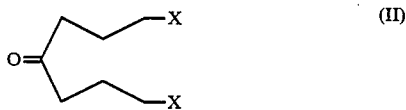

wherein X is a halogen atom or group of $R_1-SO_3$, in which $R_1$ is a hydrocarbon group,
with a cyanide of the formula

wherein $R_2$ and $R_3$ are same or different, each being hydrogen atom or a hydrocarbon group, and $R_4$ is hydroxy or amino group,
and ammonia, and if necessary, converting the compound into the salt.

While, the second concrete object of the invention can be attained by a process for the preparation of 7a-aminomethyl-2,3,5,6,7,7a-hexahydro-1H-pyrrolizine (I-A) and a salt thereof, which comprises a step for reacting 7a-cyano-2,3,5,6,7,7a-hexahydro-1H-pyrrolizine of the formula

to be obtained as above, or a salt thereof, with hydrogen in the presence of a metal catalyst, and if necessary, converting the resulting compound (I-A) into the salt.

As the salts of said compounds I-A and I-B, followings can exemplariy be listed. Hydrochloride, hydrobromide, hydroiodide, perchloride or the like hydrohalogenide; sulfate, nitrate, phosphorate or the like mineral acid salt; acetate, propionate, glycolate, maleate, fumalate, tartarate, succinate, lactate, benzoate, cinnamate or the like organic carboxylate; methanesulfonate or the like alkanesulfonate; benzenesulfonate, p-toluene sulfonate or the like arylsulfanate; cyclohexanesulfonate or the like cycloalkanesulfanate.

In the compound (II), the halogen atom may be of chlorine, bromine or iodine atom. The hydrocarbon group for the substituent $R_1$ is one selected from alkyl and aryl groups, in which as the alkyl group, methyl, ethyl, n-propyl, n-butyl, n-pentyl, n-hexyl, n-decyl or the like straight chain alkyl group having 1 to 10 carbon atoms; i-propyl, i-butyl, sec-butyl, tert-butyl, i-pentyl or the like branched chain alkyl group; cyclopropyl, cyclobutyl, cyclopentyl, cyclohexyl, cycloheptyl or the like cycloalkyl group having 3 or more carbon atoms may exemplarily be listed: and as the aryl group, phenyl, tolyl, xylyl, mesityl or the like may exemplarily be listed.

The hydrocarbon group for each of the substituents $R_2$ and $R_3$ in the compound (III) is also same with that for said substituent $R_1$.

The synthetic reaction for the compound (I-A) will be completed for 12-48 hours, when 1 to 10 equivalent amount of the compound III and 3 to 10 equivalent amount of ammonia were added, based on 1 equivalent amount of the compound (II), to stir the mixture at a temperature ranging from 20° to 50° C., in the presence or absence of a solvent. The resulting reaction mixture is made basic by adding thereto an alkali solution, and extracted with an organic solvent. After concentration of the extract, the resulting residue was distilled in vacuo to separate the desired 7a-cyano-2,3,5,6,7,7a-hexahydro-1H-pyrrolizine (Compound I-A). A salt thereof can be obtained by reacting the compound with an acid, in accordance with a manner known per se.

In the above operation procedure, an addition of ammonia in the reaction system may be carried out in any manner. Namely, the ammonia in total required amount may be dissolved in a solvent to feed same in the reaction system, ammonia gas may be blown into the reaction system, with a time interval, so as to maintain its amount in the level of 0.5 to 3 equivalent amount, the reaction may be carried out in ammonia atmosphere, or any combination thereof may be employed. As the solvent, methanol, ethanol, n-propanol, i-propanol or the like alcohol; N,N-dimethylformamide, ethyl ether, tetrahydrofuran, dioxane or the like ether may exemplarily be listed. As the alkali for making the reaction mixture basic, sodium hydrate, potassium hydrate, sodium carbonate, potassium carbonate or the like may be listed. As the extraction solvent, methylene chloride, chloroform, ethyl ether, ethyl acetate or the like may be listed.

Turning now to the raw materials, 1,7-di-substituted-4-heptanone shown by Formula II can easily be synthesized, by starting from easy available γ-butyrolactone and in accordance with the method disclosed by H. Hart et al. ["J. Am. Chem. Soc.", Vol. 78, page 112 (1956)]. Among the compounds shown by Formula III, cyanohydrine derivatives ($R_4$:OH) can easily be synthesized, in accordance with the method disclosed by Cox et al ["Org. Syn." Coll. 11, page 7 (1946)]. While, aminonitrile derivatives ($R_4$:NH$_2$) can be prepared, in accordance with the method disclosed by R. A. Jacobson et al, ["J. Am. Chem. Soc.", Vol. 68, page 2628

(1946)] and the methods disclosed in Jap. Pat. Nos. Sho 54-79232(A) and Sho 61-87658(A).

For leading 7a-cyano-2,3,5,6,7,7a-hexahydro-1H-pyrrolizine shown by Formula I-A into 7a-aminomethyl-2,3,5,6,7,7a-hexahydro-1H-pyrrolizine shown by Formula I-B, in accordance with the process of the invention, the compound I-A or its salt and a metallic catalyst, such as Raney nickel, platinum oxide, palladium carbon or the like are dissolved or suspended in a suitable solvent, and then stirred at a temperature for instance 20° C., under hydrogen gas atmosphere. It takes 6 to 24 hours, until the reaction completes. As the solvent, methanol, ethanol, n-propanol, i-propanol or the like alcohol; acetic acid, propionic acid or the like organic acid; hydrochloric acid, surfuric acid, nitric acid, perchloric acid or the like aqueous mineral acid; water; or a mixture thereof may be listed. After completion of the reaction, insoluble matters in the reaction mixture were filtered off, and the filtrate was concentrated and distilled, or after removal of the insoluble matters, the filtrate was, if necessary concentrated in vacuo, making basic with an addition of alkali solution, extracted with use of an organic solvent, concentrated the extract, and then distilled in vacuo to afford the desired compound of 7a-amonomethyl-2,3,5,6,7,7a-hexahydro-1H-pyrrolizine shown by Formula I-B. As the alkali for making the reaction mixture basic, sodium hydroxide, potassium hydroxide, sodium carbonate, potassium carbonate, sodium hydrogen carbonate or the like may be listed. As the extraction solvent, further, methylene chloride, chloroform, ethyl ether, ethyl acetate or the like may be listed.

DETAILED DESCRIPTION OF PREFERRED EMBODIMENTS

The invention will now be further explained in more detail with reference to Examples.

EXAMPLE 1

7a-Cyano-2,3,5,6,7,7a-hexahydro-1H-pyrrolizine

To a solution of aceton cyanohydrin (2.3 g, 27 mmol) saturated with ammonia, 1,7-dichloro-4-heptanone (0.50 g, 2.7 mmol) was added dropwise at 20° C. The resulting solution was stirred for 48 hours at 20° C. under ammonia gas atmosphere. To the reaction mixture, 0.1N-NaOH was added to extract with methylene chloride. The extract was dried over anhydrous sodium sulfate, concentrated and distilled in vacuo to afford 0.33 g of the desired compound (Yield: 89%).

Boiling point: 70°–74° C. (3 mmHg).

$^1$H-NMR spectrum (CDCl$_3$–) δ ppm: 1.73–2.47 (8H, m,

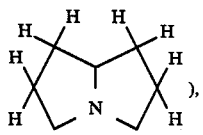

2.47–2.77 (2H, m, 3.03–3.40 (2H, m,

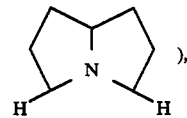

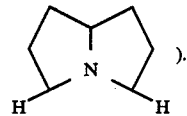

IR spectrum ($\nu_{max}^{neat}$) cm$^{-1}$: 2960, 2860, 2810 (C—H), 2225 (C—N).

MS spectrum (EI/DI) m/z: 136 (M+).

EXAMPLE 2

7a-Cyano-2,3,5,6,7,7a-hexahydro-1H-pyrrolizine

A mixed solution of 2-amino-2-methylpropanenitrile (41.4 g, 492 mmol) and 1,7-dichloro-4-heptanone (30.0 g, 164 mmol) in 220 ml of 16% NH$_3$/MeOH solution was stirred for 24 hours at 20° C. The resulting reaction mixture was concentrated in vacuo to remove MeOH therefrom, added 0.1N NaOH to the residue, which was extracted with methylene chloride, and the extract was dried over anhydrous sodium sulfate, concentrated, and distilled in vacuo to afford 18.1 g of the desired compound (Yield: 82%).

Physical data of the compound is same with those in Example 1.

EXAMPLE 3

7a-Aminomethyl-2,3,5,6,7,7a-hexahydro-1H-pyrrolizine

In 8.5 ml of acetic acid introduced therein hydrogen chloride gas (400 mg, 11.0 mmol), 7a-cyano-2,3,5,6,7,7a-hexahydro-1H-pyrrolizine (300 mg, 2.20 mmol, obtained in Example 1) and platinum oxide (30 mg) were added to stir under hydrogen gas atmosphere for 24 hours at 20° C. After removal of insoluble matters from the reaction mixture, the filtrate was concentrated, 0.5N NaOH (10 ml) was added to the residue, which was extracted with chloroform, the extract was dried over anhydrous sodium sulfate, concentrated, and distilled in vacuo to afford 188 mg of the desired compound (Yield: 61%).

Boiling point: 46°–49° C. (3 mmHg).

$^1$H-NMR spectrum (CDCl$_3$) δ ppm: 1.40 (2H, br.s, NH$_2$), 1.49–1.83 (8H, m,

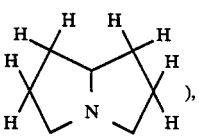

2.53 (2H, s, CH$_2$NH$_2$), 2.60–2.66 (2H, m,

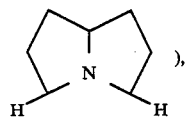

2.93–3.02 (2H, m,

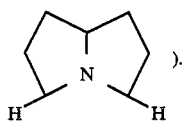

IR spectrum ($\nu_{max}^{neat}$) cm$^{-1}$: 3380 (N—H), 2950 (C—H), 1460, 1100, 840.

MS spectrum (EI/DI) m/z: 110 (base peak).

MS spectrum [CI/DI (i-Bu)] m/z: 141 [(M+1)$^+$].

What is claimed is:

1. A process for the preparation of 7a-cyano-2,3,5,6,7,7a-hexahydro-1H-pyrrolizine of the formula

 (I-A)

and a salt thereof, which comprises a step of reacting 1,7-di-substituted-4-heptanone of the formula

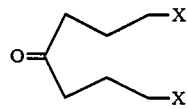 (II)

wherein X is a halogen atom or group of $R_1$—SO$_3$, in which $R_1$ is a hydrocarbon group, with a cyanide of the formula

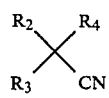 (III)

wherein $R_2$ and $R_3$ are same or different, each being hydrogen atom or a hydrocarbon atom, and $R_4$ is hydroxy or amino group, and ammonia, and if necessary, converting the compound into the salt.

* * * * *